United States Patent [19]

Margel

[11] Patent Number: 4,624,923
[45] Date of Patent: Nov. 25, 1986

[54] METAL-COATED POLYALDEHYDE MICROSPHERES

[75] Inventor: Shlomo Margel, Rehovot, Israel

[73] Assignee: Yeda Research and Development Company Limited, Rehovot, Israel

[21] Appl. No.: 822,774

[22] Filed: Jan. 24, 1986

Related U.S. Application Data

[63] Continuation-in-part of Ser. No. 618,494, Jun. 8, 1984, abandoned.

[51] Int. Cl.$^4$ ............................................. C12N 11/14
[52] U.S. Cl. ................................. 435/176; 427/222;
428/407; 424/1.1; 424/85; 424/88; 424/94;
436/526; 436/528; 436/531; 436/532; 436/533;
521/53; 521/55; 521/57; 521/186; 521/153
[58] Field of Search .................. 521/53, 84.1, 57, 55;
428/407; 427/222; 524/17; 424/1.1, 85, 88, 94

[56] References Cited

U.S. PATENT DOCUMENTS

| | | | |
|---|---|---|---|
| 3,957,741 | 5/1976 | Rembaum et al. | 526/312 |
| 4,035,316 | 7/1977 | Yen et al. | 526/225 |
| 4,138,383 | 2/1979 | Rembaum et al. | 526/320 |
| 4,197,220 | 4/1980 | Rembaum et al. | 525/354 |
| 4,267,235 | 5/1981 | Rembaum et al. | 528/245 |
| 4,413,070 | 11/1983 | Rembaum | 523/223 |

Primary Examiner—Morton Foelak
Attorney, Agent, or Firm—John P. White

[57] ABSTRACT

A metal-containing polyaldehyde microsphere composed of a polyaldehyde microsphere to which a transition metal, e.g. Au, Ag, Pt, Pd, Tc, Fe, Ni or Co, is bound may be obtained in accordance with this invention. The polyaldehyde, e.g. polyacrolein or polyglutaraldehyde, may be encapsulated in agarose, and the microsphere may be radioactive or magnetic. The microphere may additionally have a compound having at least one amine group, e.g. a drug, antibody, antigen, enzyme or other protein, bound to its surface.

In one embodiment a transition metal is bound to a polyaldehyde microsphere by contacting the polyaldehyde microsphere with a suitable amount of an appropriate salt or acid of the transition metal under suitable conditions so as to cause the salt or acid to be reduced to a lower valence state and to bind to the microsphere. Some salts or acids may thus be reduced to the elemental state; others are further reduced with an appropriate reducing agent.

In another embodiment, a transition metal in elemental form is bound to a polyaldehyde microsphere by contacting the polyaldehyde microsphere with a suitable amount of a compound capable of complexing with a salt or acid of the transition metal under suitable conditions permitting binding of the compound to the microsphere, contacting the compound with an appropriate amount of an appropriate salt or acid of a transition metal under appropriate conditions permitting the compound to bind to the salt or acid, and reducing the salt or acid to the corresponding elemental metal by contacting it under effective reducing conditions and for a sufficient period of time with a sufficient amount of an effective reducing agent.

The metal-containing microsphere of this invention is useful for such applications as cell labeling, cell separation, diagnostic methods, catalysis and coating methods.

9 Claims, No Drawings

METAL-COATED POLYALDEHYDE MICROSPHERES

This application is a continuation-in-part of U.S. Ser. No. 618,494, filed June 8, 1984, now abandoned, the contents of which are hereby incorporated by reference.

BACKGROUND OF THE INVENTION

The synthesis of inorganic metal colloidal particles, e.g., colloidal particles of Ag, Au, and Co, has been described in numerous publications. Proteins can be absorbed quite strongly onto the surface of these metal colloids. The protein-metal particles possess many biological applications, including cell labeling, cell separation and diagnostics, Cais, M. et al., Nature 270:534 (1974); Poynton, C. H. et al., Lancet 1:524 (Mar. 5, 1983).

The synthesis of polymeric microspheres containing metals has been disclosed in several patents, e.g. Yen et al., U.S. Pat. No. 4,157,323, issued June 5, 1979 at Col. 2, lines 37-56 and Col. 6, lines 22-38; Rembaum et al., U.S. Pat. No. 4,267,235, issued May 12, 1981 at Col. 2, lines 42-46, Col. 3, lines 32-34 and Col. 3, line 51-Col. 4, lines 10; and Rembaum, U.S. Pat. No. 4,413,070, issued Nov. 1, 1983, at Col. 3, line 65-Col. 4, line 1 and Col. 6, line 12-41, as well as in West German Application No. P3224484.3, filed June 30, 1982 in the name of Yeda Research and Development Co., Ltd., and published Jan. 20, 1983. These metal-containing microspheres were obtained by entrapping the metal during the polymerization process. Polymeric microspheres so produced and which contain iron particles were used primarily for cell separation via a magnetic field. The synthesis of polyamino microspheres containing various metals, e.g. metal-containing polyvinyl pyridine copolymeric microspheres, is disclosed in Rembaum et al., U.S. Pat. No. 4,197,220, issued Apr. 8, 1980 at Col. 3, lines 3-20, 41-50 and Col. 5, line 31, Col. 6, line 10.

Various types of polyaldehyde microspheres and their syntheses are known, e.g. polyglutaraldehyde microspheres, Rembaum et al., U.S. Pat. No. 4,267,235; polyacrolein microspheres, W. German Application No. P 3224484.3 (via base catalysis, redox initiation or irradiation initiation) and Rembaum, U.S. Pat. No. 4,413,070 (irradiation initiation) and agarose encapsulated polyaldehyde microsphere beads, European Application No. 83 101 88 3.3, filed Feb. 25, 1983 in the name of Yeda Research and Development Co., Ltd., and published Sept. 7, 1983. Polyacrolein microspheres and agarose-polyacrolein microsphere beads are additionally disclosed in several papers including Margel, Beitler and Offarim, Immunological Commun. 10 (7): 567-575 (1981); Margel, Ind. Eng. Prod. Res. Dev. 21: 343-348 (1982); Margel, Beitler and Offarim, J. Cell Science 56: 157-175 (1982); Marcus, Offarim and Margel, Biomat., Med. Dev., Art. Org. 10(3): 157-171 (1982); Margel, FEBS Letters 145(2):341-344 (1982) and Margel and Offarim, Analyt. Biochem. 128: 342-350 (1983).

Of the above-mentioned patents and patent applications U.S. Pat. No. 4,413,070 at Col. 3, lines 62-64 and Col. 8, lines 27-32 and European Application No. 83 101 88 3.3, P. 12, example 22 also disclose the use of various microspheres to chelate salts or other metal-containing compounds. See also Margel, FEBS Letters 145(2):341-344 (1982); Margel and Hirsh, Biomat., Med. Dev., Art. Org. 9(2):109-125 (1982); and Margel, J. Med. Chem. 24(10):1263-1266(1981).

Heretofore, however, polymeric microspheres containing elemental metals and aldehyde groups available for convenient derivatization of the microspheres with amino ligands have not been disclosed.

It is therefore an object of the present invention to provide such metal-containing polyaldehyde microsphere. It is an additional object of this invention to provide methods for preparing such microspheres. It is a further object of this invention to provide methods for using such microspheres in various applications.

SUMMARY OF THE INVENTION

A metal-containing polyaldehyde microspheres composed of a polyaldehyde microsphere to which a transition metal, in elemental form is bound may be obtained in accordance with this invention. The polyaldehyde microsphere may be encapsulated in agarose, and the polyaldehyde is preferably polyacrolein or polyglutaraldehyde. Preferred transition metals include gold, silver, platinum, palladium, technetium, iron, nickel and cobalt. The metal may be a radioactive isotope or may be magnetic. A metal-containing polyaldehyde microsphere of this invention may additionally have a compound having at least one primary amine group bound to it. Such a compound may be a drug, antibody, antigen, enzyme or other protein. In a preferred embodiment, the compound is an antibody.

In one embodiment the transition metal may be bound to a homogeneous polyaldehyde microsphere by a process which includes contacting the polyaldehyde microsphere with a suitable amount of an appropriate salt or acid of the transition metal under suitable conditions and for a sufficient period of time so as to cause the salt or acid of the transition metal to be reduced to a lower valence state by the aldehyde groups of the microsphere and to bind to the microsphere. The polyaldehyde microsphere may be encapsulated in agarose and is preferably a homogeneous microsphere composed of polyacrolein or polyglutaraldehyde. Preferred transition metals include gold, silver, platinum or palladium, and their radioactive isotopes. In a presently preferred embodiment the amount of the salt or acid of the transition metal is about 1 to 6 times the dry weight of the microsphere. Suitable conditions for this process include a pH value between about 2 and 10 and a temperature of up to about 70° C. A sufficient period of time for the reaction may be as short as one hour or as long as three months, depending on the metal compound and reaction temperature used. In some cases, e.g., in the case of Au and Ag, the metal is reduced to the elemental state. To achieve reduction to the elemental state in other cases, or to complete the reduction in a shorter time, the salt or acid bound to the microsphere is contacted under effective reducing conditions with a suitable amount of an appropriate reducing agent, e.g. sodium borohydride in an amount of about two times the dry weight of the microsphere. Effective reducing conditions for the process using sodium borohydride include a temperature of about 0°-25° C., e.g. 4° C., and the appropriate period of time is from about 1 to 3 hours.

In another embodiment a transition metal in elemental form is bound to a polyaldehyde microsphere by contacting the polyaldehyde microsphere with a suitable amount of a compound containing at least one primary amine group under suitable conditions permitting binding of the compound to the microsphere, the compound being capable of binding to the microsphere and of complexing with a salt or acid of the transition metal; contacting the compound with an appropriate amount of an appropriate salt or acid of the transition metal under appropriate conditions permitting the compound to complex with the salt or acid and reducing the salt or acid to the corresponding elemental metal by contacting it under effective reducing conditions and for a sufficient period of time with a sufficient amount of an effective reducing agent, e.g., sodium borohydride.

The polyaldehyde microsphere used in this process also may be encapsulated in agarose and is preferably composed of polyacrolein or polyglutaraldehyde. The preferred transition metals include gold, silver, platinum, palladium, technetium, iron, nickel and cobalt and may be a radioactive isotope or magnetic. Presently preferred compounds capable of binding to the microsphere and of complexing with the salt or acid of the transition metal include deferoxamine, hexanediamine, polyethylene imine and N,N-diethylethylenediamine, suitably in an amount from about 10% to about 150% of the dry weight of the microsphere. An appropriate amount of the salt or acid for use in this process is from about 40% to about 150% of the dry weight of the microsphere. Suitable conditions permitting binding of the compound to the microsphere include a pH value between about 3.0 and 11.0 and a temperature of up to about 70° C., e.g. 60° C. Appropriate conditions permitting the compound to bind the salt or acid include a temperature from ambient temperature up to about 40° C. An effective reducing agent in this process is sodium borohydride, a sufficient amount of which by weight is about two times the dry weight of the microsphere. Effective reducing conditions for the use of sodium borohydride in this process include a temperature of about 0°-10° C., e.g. 4° C., and a sufficient period of time is at least about one hour.

Thus, by the processes of this invention a metal-containing polyaldehyde microsphere may be obtained and may be magnetic or radiolabeled. Additionally the microsphere may be bound to a compound containing at least one primary amine group, e.g., a drug, antibody, antigen, enzyme or other protein.

One embodiment of this invention is a method of labeling a cell which involves contacting the cell with a metal-containing polyaldehyde microsphere which additionally has a compound, e.g. an antibody, bound to its surface, the compound, e.g. an antibody, being capable of binding to the cell under suitable conditions.

Another embodiment is a method of separating one type of cell from other types of cells which involves contacting the cells with magnetic microspheres of this invention having bound to them a compound, e.g. antibody, capable of binding to the desired type of cells under suitable conditions and recovering cells bound to the magnetic microspheres.

Another embodiment is a diagnostic method for detecting in a biological fluid the presence of an agent associated with a disorder which involves contacting the fluid with a microsphere of this invention having bound to it an antibody capable of reacting with the agent under suitable conditions and determining the occurrence of the reaction.

A further embodiment is a method of catalyzing a chemical reaction capable of being catalyzed by a transition metal which involves conducting the reaction in the presence of a catalytically effective amount of metal-containing polyaldehyde microspheres of this invention.

Still another embodiment is a method for coating various supports with the metal-containing microspheres which involves preparing a suspension of the microspheres in an appropriate solvent, coating the support with the suspension and evaporating the solvent.

DETAILED DESCRIPTION OF THE INVENTION

A metal-containing polyaldehyde microsphere composed of a polyaldehyde microsphere to which a transition metal in elemental form is bound may be obtained in accordance with this invention. In one embodiment, the microsphere is encapsulated in agarose. Agarose encapsulated beads of this type suitably have a diameter between about 40$\mu$ and 1200$\mu$ and are compatible with sensitive biological systems such as blood serum.

Suitable polyaldehydes in accordance with this invention are numerous and varied, and include all polyaldehydes which can be prepared in the form of powders or microspheres, preferably as microspheres having a diameter between about 0.01$\mu$ and 100$\mu$. Especially preferable are microspheres having a diameter between about 0.04$\mu$ and about 5.0$\mu$. Preferably the polyaldehyde is polyacrolein, polymethacrolein, polycrotonaldehyde or polyglutaraldehyde. Polyacrolein and polyglutaraldehyde are especially preferred. Homopolymers and copolymers known in the art, e.g., with acrylates, acrylamides, vinyl pyridines and their derivatives as comonomers, are suitable for use in accordance with this invention. Preferably, however, the polyaldehyde is a homopolymer.

Presently preferred transition metals for binding in elemental form to the microsphere of this invention include gold, silver, platinum, palladium, technetium, iron, nickel and cobalt. The metal may be a radioactive isotope or may be magnetic.

In one embodiment of this invention the metal-containing polyaldehyde microsphere additionally has a compound having at least one primary amine group bound to its surface.

Depending on the intended use for the microsphere the compound may be a drug, antibody, antigen, enzyme or other protein. Antibodies in particular, including both serum and monoclonal antibodies, when bound to a microsphere of this invention provide useful reagents for numerous biochemical and medical applications, including cell labeling, cell separation and diagnostic methods. Such a microsphere may also be magnetic as well. In biological applications, the presence of the more inert, elemental metal rather than metal of a higher oxidation state may be advantageous where sensitive biochemical systems are present.

Two general approaches are used to prepare the metal-containing microspheres of this invention. Both involve binding a salt or acid of the desired transition metal to the preformed polyaldehyde microsphere and reducing the metal moiety to the elemental form of the metal. This is in contrast to the methods for producing the prior art metal-containing microspheres which involve polymerization in the presence of a metal compound, thereby entrapping the metal compound within the microsphere so produced. By the methods of this invention numerous and varied metals may be attached to the microspheres without adding undue complexity and the attendant possibility of undesired side reactions to the polymerization reaction mixture.

One process of the subject invention for binding a transition metal to the polyaldehyde microsphere involves contacting the polyaldehyde microsphere with a suitable amount of an appropriate salt or acid of the transition metal under suitable conditions and for a sufficient period of time so as to cause the salt or acid to be reduced to a lower valence state by the aldehyde groups of the microsphere and to bind to the microsphere.

Suitable microspheres for use in this and other embodiments of this invention include polyaldehyde microspheres which are encapsulated in agarose such as those disclosed in Marcus, Offarim and Margel, Biomat., Med. Dev., Art. Org. 10(3):157-171(1982); Margel, FEBS Letters 145(2): 341-344(1982); Margel and Offarim, Analytical Biochem. 128:342-350(1983) and European Patent Application No. 83101883.3, filed Feb. 25, 1983 in the name of Yeda Research and Development Co. Ltd., and published Sept. 7, 1983.

Suitable polyaldehydes for use in this and other embodiments of the invention are numerous and varied, and include all polyaldehydes which can be prepared in the form of microspheres, preferably having a diameter between about $0.01\mu$ and $100\mu$. Especially preferable are microspheres having a diameter between about $0.04\mu$ and $5.0\mu$. Preferably the polyaldehyde is polyacrolein, polymethacrolein, polycrotonaldehyde or polyglutaraldehyde. Polyacrolein and polyglutaraldehyde are especially preferred.

Suitable polyacrolein and polyacrolein-type microspheres for use in this invention may be obtained by methods disclosed in Margel, Beitler and Offarim, Immunol. Communications 10(7):567-575(1981); Margel, Beitler and Offarim, J. Cell Sci. 56:157-175(1982); Margel, Ind. Eng. Chem. Prod. Res. Dev. 21:343-348(1982); W. German Patent Appn. No. P3224484.3, filed June 30, 1982 in the name of Yeda Research and Development Co. Ltd., and published Jan. 20, 1983 and Rembaum, U.S. Pat. No. 4,413,070, filed Mar. 30, 1981 and issued Nov. 1, 1983.

Both homopolymeric and copolymeric microspheres are suitable for use in this invention. Copolymeric polyacrolein microspheres and their preparation are disclosed in published W. German Patent Application P3224484.3 and U.S. Pat. No. 4,413,070, both of which are cited above. Presently preferred however, are homopolymeric microspheres.

Suitable polyglutaraldehyde microspheres for use in this invention may be obtained by the methods of Rembaum and Margel, U.S. Pat. No. 4,267,235, filed Mar. 19, 1979 and issued May 12, 1981.

Transition metals preferred for use in accordance with this method include gold, silver, platinum and palladium. The metal may be a radioactive isotope. Appropriate salts or acids of such metals include those which may be conveniently reduced, e.g., $NaAuCl_4$ or $HAuCl_4$; $AgNO_3$, especially with $NH_3$; $H_2PtCl_6$ and $PdCl_2$.

In synthesizing the metal containing polyaldehyde microspheres, the suitable amount of the salt or acid of the transition metal may be varied depending on how much metal one wishes to bind to the microspheres, which in turn depends on the intended use for the microspheres. A smaller relative amount of a radioisotope may be used, for instance, to impart a discreet radiolabel to the microspheres. Larger relative amounts of an appropriate metal material may be used to produce microspheres which are more intensely radiolabeled or colored or especially electron-dense. In any case, the process is operative over a wide range of concentrations of the metal material. It is limited only in that each microsphere contains a finite number of aldehyde groups to interact with the metal material. In a presently preferred embodiment the suitable amount of the salt or acid of the transition metal is about 1 to 6 times the dry weight of the microspheres.

Similarly, a wide range of reaction conditions may be employed in producing the metal containing micropheres. pH values, for example, selected from between about 2 and about 10 are used in several of the preferred embodiments of this invention, as are reaction temperatures up to about 70° C. Depending on the particular salt or acid and the reaction temperature, a sufficient period of time for the reaction of the metal material and the polyaldehyde microsphere may be as short as one hour or as long as three months. Elevating the reaction temperature generally permits shorter reaction times. Reaction progress can often be monitored qualitatively by observing a color change indicating that the salt or acid of the metal has been reduced in the presence of the polyaldehyde microsphere. Those of ordinary skill in the art will appreciate that the particular color change observed will depend on the particular metal involved. Silver, palladium and platinum, for example, have resulted in black microspheres, while gold has resulted in purple microspheres.

In some cases, e.g. in the case of silver and gold compounds, the metal may be reduced to the elemental state by the above-described process. To achieve complete reduction, i.e., to the elemental state, in other cases or to complete the reduction in a shorter time, the partially reduced metal salt or acid bound to the microsphere may be contacted with a suitable amount of an appropriate reducing agent under effective reducing conditions. Appropriate reducing agents include borohydride reagents, e.g. sodium borohydride ($NaBH_4$). The suitable amount of the borohydride reagent will depend on the quantity and oxidation state of metal to be reduced. In presently preferred embodiments a suitable amount of sodium borohydride is about two times the dry weight of the microsphere. Suitable conditions for the borohydride reduction include a temperature of about 0°-25° C., e.g. 4° C., and an appropriate period of time is from about 1 to 3 hours.

In another aspect of this invention a transition metal in elemental form is bound to a polyaldehyde microsphere in a process involving contacting the polyaldehyde microsphere with a suitable amount of a compound containing at least one primary amine group, under suitable conditions permitting binding of the compound to the microsphere, the compound being capable of binding to the microsphere and of complexing with a salt or acid of the transition metal; contacting the compound with an appropriate amount of an appropriate salt or acid of the transition metal under appropriate conditions permitting the compound to bind to the salt or acid; and reducing the salt or acid to the corresponding elemental metal by contacting it under effective reducing conditions and for a sufficient period of time with a sufficient amount of an effective reducing agent.

A polyaldehyde microsphere which is encapsulated in agarose is also suitable for use in this process. Such agarose encapsulated microspheres are disclosed in, e.g., Margel, Anal. Biochem. 128:342–350 (1983) and published European Appln. No. 83101883.3. Suitable polyaldehydes are, again, those mentioned above, i.e., those which can be prepared in the form of microspheres, preferably having a diameter between about 0.01 and 100 microns. Especially preferable are microspheres having a diameter between about 0.04 and 5.0. The polyaldehyde is suitably polyacrolein, polymethacrolein, polycrotonaldehyde or polyglutaraldehyde, e.g., as disclosed by Margel or Rembaum or both in the previously cited papers, patents and published applications. Polyacrolein and polyglutaraldehyde are presently preferred polyaldehydes. Both homopolymeric and copolymeric polyaldehyde microspheres are suitable for use in this process, although homopolymeric microspheres are again preferred.

Transition metals which are preferred for use in this process include gold, silver, platinum, palladium, technetium, iron, nickel and cobalt. The metal may be a radioactive isotope or may be magnetic.

Compounds suitable for use in this method include those compounds capable of binding to a polyaldehyde microsphere and complexing with a salt or acid of a transition element. Preferably the compound contains at least one primary amine group, e.g., deferoxamine (or desferal, the mesylate salt thereof); and may be a diamine such as hexanediamine or N,N-diethylethylenediamine, or a polyamine, such as polyethlene imine. The amount of the compound used may be varied widely depending upon the amount of metal one wishes to bind to the microsphere and the specific compound used. In presently preferred embodiments the amount of the chelating compound is from about 10% to about 150% of the dry weight of the microsphere, again, depending on the extent of the derivitization desired. An appropriate amount of the salt or acid will depend on the amount of chelating compound bound to the microsphere. In presently preferred embodiments the amount is from about 40% to about 150% of the dry weight of the microsphere. Suitable conditions permitting binding of the compound to the microsphere are relatively flexible. In presently preferred embodiments the suitable pH is a value between about 3.0 and 11.0 and the reaction temperature may be up to about 70° C. In one embodiment the temperature is about 50°–70° C., e.g., 60° C. and the reaction is complete generally within 12 hours.

Complexing of the compound with the salt or acid is effected by contacting the compound bound to the microsphere with an appropriate amount of an appropriate salt or acid of a transition metal under appropriate conditions permitting the compound to complex with the salt or acid. As noted above, an appropriate amount of salt or acid in presently preferred embodiments is from about 40% to about 150% of the dry weight of the microsphere. Appropriate conditions permitting the compound to bind to the salt or acid vary depending on the compound bound to the microsphere and the metal compound to be complexed. Preferably the conditions comprise a temperature from ambient temperature up to about 60° C., e.g., 40° C. The salt or acid thus complexed with the compound bound to the microsphere is then reduced to the corresponding elemental metal by contacting it under effective reducing conditions and for a sufficient period of time with a sufficient amount of an effective reducing agent. While various reducing agents may be employed, borohydride reagents, e.g. $NaBH_4$, are preferred. The sufficient amount of $NaBH_4$ will again depend on the amount and oxidation state of the metal to be reduced. In presently preferred embodiments the amount of $NaBH_4$ is about two times the dry weight of the microsphere. Effective reducing conditions in preferred embodiments include a temperature of about 0°–25° C., e.g. about 4° C., and a sufficient period of time for completion of the reaction is at least about one hour.

By these processes a metal-containing polyaldehyde microsphere of this invention is produced. The microsphere may be radioactive or magnetic and, may also have bound to it a compound containing at least one primary amine group. Binding to an amino compound, e.g., a drug, antibody, antigen, enzyme or other protein, is readily effected by contacting the metal-containing microsphere with the compound at a temperature of up to 70° C. for up to about 12 hours. Where the compound is sensitive to elevated temperatures, however, binding may be conducted readily at reduced temperature, e.g. at about 4° C. in about 2 hours. Alternatively, the compound containing the primary amine group may be bound to the polyaldehyde microsphere under the same reaction conditions, but before the transition metal is bound to the microsphere. It should be understood that where the microsphere is bound to the metal via a compound capable of complexing with a metal salt or acid that the drug, antibody, antigen, etc. will constitute a second compound containing at least one primary amine group which is bound to the microspheres.

The metal-containing microspheres of this invention are useful in a variety of applications. One embodiment of this invention is a method of labeling a cell which involves contacting the cell with a metal-containing polyaldehyde microsphere, the microsphere having bound to it a compound being capable of binding to the cell under suitable conditions. Mouse splenocytes, for example, may be labeled by this method with gold-containing polyacrolein microspheres of 0.1 average diameter which have bound to them goat antimouse antibodies. The splenocytes are labeled by shaking them with the microspheres at 4° C. for one hour. The splenocytes labeled by this method are dark red in color when viewed under a microscope.

Another embodiment is a method of separating one type of cell from other types of cells. The method involves contacting the cells with magnetic metal-containing polyaldehyde microspheres of this invention having bound to them a compound capable of binding to the desired type of cell under suitable conditions and recovering the cells bound to the magnetic microspheres. Preferably the compound is an anbibody. By this method human red blood cells may be separated from turkey red blood cells using iron-containing polyacrolein microspheres which have goat antirabbit IgG bound to them. In accordance with this method a mixture of turkey red blood cells and human red blood cells first treated with rabbit anti-human red blood cell antibody were shaken with the goat anti-rabbit derivatized microspheres. The mixture was then separated in a magnetic field. By this method cells bound to the magnetic microspheres were separated, and more than 95% of the separated cells were found to be human red blood cells.

An additional embodiment of this invention is a diagnostic method for detecting in a biological fluid the presence of an agent associated with a disorder. This method involves contacting the fluid with a metal-containing microsphere of this invention which additionally has bound to it an antibody capable of reacting with the agent under suitable conditions and determining the occurrence of the reaction. By this method, for example, human chorionic gonodotropin (HCG) may be detected in urine with gold-containing microspheres which have bound to them rabbit anti-human chorionic gonadotropin antibody. The agglutination reaction between the microsphere-bound antibody and the HCG in the urine results in a color change in the suspension which can be measured spectrophotometrically, and correlated with the presence of the agent, HCG.

An additional application of the microspheres of this invention involves a method for catalyzing a chemical reaction capable of being catalyzed by a transitional metal. In accordance with this method the chemical reaction is conducted in the presence of a catalytically effective amount of polyaldehyde microspheres to which an appropriate transition metal in elemental form is bound. By this method the hydrogenation of double bonds may be effected with hydrogen gas at ambient temperature and pressure in the presence of platinum-containing microspheres.

A further use of the microspheres of this invention is in a method for coating a support with metal-containing polyaldehyde microspheres. According to this method a suspension of the microspheres is prepared in an appropriate solvent. The support is coated with the suspension and the solvent is evaporated. By this method films of various thicknesses may be prepared which may then be used in place of the free microspheres.

This invention is illustrated in the examples which follow. The examples are set forth to aid in an understanding of the invention but are not intended to, and should not be construed to, limit in any way the invention as set forth in the claims which follow thereafter.

EXAMPLES

Materials

The various polyacrolein and polyacrolein-type microspheres used in the following examples may be obtained by the methods disclosed in S. Margel, Ind. Eng. Chem. Prod. Res. Dev. 21:343-348 (1982); S. Margel, U. Beitler and M. Offarim, Immunol. Commun. 10(7):567-575 (1981) and A. Rembaum, U.S. Pat. No. 4,413,070, issued Nov. 1, 1983. The terms "alkaline," "irradiated," and "redox" as used herein refer to the polymerization methods used in preparing the microspheres.

Polyglutaraldehyde microspheres may be obtained by the method of A. Rembaum and S. Margel, U.S. Pat. No. 4,267,235, issued May 12, 1981.

Agarose encapsulated polyaldehyde microspheres may be obtained by the methods of L. Marcus, M. Offarim and S. Margel, Biomat., Med. Dev., Art. Org., 10(3):157-171 (1982); S. Margel, FEBS Letters 145(2):341-344; and S. Margel and M. Offarim, Anal. Biochem. 128:342-350 (1983).

Other materials were purchased from commercial sources: $NaAuCl_4$, $HAuCl_4$ and hydroquinone (Fluka AG, Buchs SG). $AgNO_3$, $CoCl_2$, $NiCl_2$, $NaBH_4$, $Fe_2(SO_4)_3$, platinum black and hexane diamine (Aldrich, Milwaukee, Wis.), $H_2PtCl_6$ and $PdCl_2$ (Merck, Darmstadt, W. Germany), deferoxamine (Ciba-Geigy Pharmaceuticals, Bazel, Switzerland), polyethylene imine (Polysciences, Warrington, Pa.), N,N,-diethylethylenediamine, and bovine serum albumine (Sigma, St. Louis, Mo.), goat IgG, goat anti-mouse IgG, goat anti-rabbit IgG, anti Thy 1.2, human chorionic gonadotropin and rabbit anti-human chorionic gonadotropin (Miles yeda, Rehovot, Israel), ethanol and polyvinyl chloride (Frutarom, Haifa, Israel), sepharose 4B (Pharmacia Fine Chemicals, Uppsala, Sweden). Spectrophotometric measurements were achieved with Uvikon 810, Kontron Spectrophotometer, Switzerland.

All suspensions and solutions are aqueous unless otherwise indicated.

Preparations of the Metal Coated Microspheres

EXAMPLE 1

Monodisperse "alkaline" polyacrolein microspheres (50 mg in 2 ml $H_2O$) of 1 average diameter were added to 100 ml of an aqueous solution containing 50 mg $NaAuCl_4$ (or $HAuCl_4$) at pH 7.0. The mixture was then shaken for 2 weeks at room temperature. During this time an intense purple color developed. The coated microspheres thus produced were washed by four centrifugations at 500 g for 10 min. and could then be redispersed in $H_2O$ or in PBS. The aldehyde content of the microspheres decreased during the coating procedure from 2.9 millimole/g microspheres to 2.1 millimole/g microsphers. The gold content in the resulting microspheres was 9% (w/w).

EXAMPLE 2

Gold coated microspheres prepared as described in example 1 were added to 200 ml of an aqueous solution containing 100 mg $NaAuCl_4$ (or $HAuCl_4$) at pH 7.2. The mixture was then shaken for an additional two weeks at room temperature. The intensely colored purple microspheres were washed by four centrifugations at 500 g for 10 min. The aldehyde content of gold coated microspheres so obtained decreased further to 1.4 millimole/g microspheres. The gold content in the resulting microspheres was 19% (w/w). A further addition of the gold compound (500 mg in 500 ml $H_2O$ and a reaction time of two weeks) resulted in gold coated microspheres with a negligible aldehyde content.

EXAMPLE 3

Examples 1 and 2 were repeated substituting for the "alkaline" polyacrolein microspheres ($1\mu$ diameter) the following polyaldehyde microspheres: "Alkaline" polyacrolein microspheres (cross linked and not cross linked) of $0.1\mu$ and $5\mu$ diameters, "irradiated" polyacrolein microspheres of $0.1\mu$ average diameter. Polyglutaraldehyde microspheres of $0.4\mu$ average diameter and agarose-polyacrolein microsphere beads of diameters ranging from $40\mu$ to $200\mu$ and from $800\mu$ to $1200\mu$. The polyacrolein and polyglutaraldehyde microspheres were washed by four centrifugations. The agarosepolyacrolein microsphere beads were washed by repeated decantation. The aldehyde content of these microspheres decreased proportionately as described in experiments 1 and 2.

EXAMPLE 4

Example 1 was repeated at 60° C. for 24 h. Similar aldehyde content of the microspheres was obtained.

EXAMPLE 5

Example 1 was repeated at pH 2.4. Similar aldehyde content of the microspheres was obtained.

EXAMPLE 6

Example 1 was substituting for water aqueous ethanol (10%) solution. Similar aldehyde content of the microspheres was obtained.

EXAMPLE 7

Examples 1, 2 and 4 were repeated substituting for the polyacrolein microspheres polyacrolein powder. Similar aldehyde contents were obtained.

EXAMPLE 8

0.5 g $AgNO_3$ in 2 ml $H_2O$ was added to 5 ml of an aqueous solution containing 100 mg of "irradiated" polyacrolein microspheres of $0.1\mu$ average diameter and 5 $\mu l$ hydroquinone. An aqueous ammonia solution was added stepwise until pH 10 was reached. The solution was shaken for 1 hour. Then, the silver coated microspheres were washed by three centrifugations at 2000 g for 10 minutes. The microspheres could then be redispersed in $H_2O$ or in PBS in the presence of 0.05% (w/v) hydroquinone. The aldehyde content of these microspheres decreased as a result of the coating procedure from 9.3 millimole/g microspheres to 7.3 millimole/g microspheres. The silver content of the resulting microspheres was 40% (w/w).

EXAMPLE 9

Example 8 was repeated substituting for the "irradiated" microspheres the following polyaldehyde microspheres: "alkaline" polyacrolein microspheres of $1\mu$ and $5\mu$ diameters, polyglutaraldehyde microspheres of $0.4\mu$ average diameter and agarose-polyacrolein microsphere beads of diameters ranging from $40\mu$ to $200\mu$ and from $800\mu$ to $1200\mu$. The microspheres were washed as described in example 3. The aldehyde content of these silver coated beads decreased proportionately as described in Example 8.

EXAMPLE 10

Monodisperse "alkaline" polyacrolein microspheres (50 mg in 2 ml $H_2O$) of $1\mu$ diameter were added to 100 ml of an aqueous solution containing 300 mg $H_2PtCl_6$ at pH 7.0. The mixture was shaken for three months at room temperature. During this time an intense black color developed. The platinum coated microspheres were washed as described in Example 1. The aldehyde content of the microspheres decreased as a result of the coating procedure from 2.9 millimole/g microspheres to 2.2 millimole/g microspheres. The platinum content of the resulting microspheres was 7% (w/w).

EXAMPLE 11

Example 10 was repeated at pH 2.0. The aldehyde content decreased similarly.

EXAMPLE 12

The experiment described in Example 10 was carried out for 48 hours. The microspheres were then washed by three centrifugations at 500 g for 10 minutes. Thereafter, the microspheres were redispersed in $H_2O$. The metal contained on the microspheres was reduced to the elemental state by adding 100 mg $NaBH_4$ to the microsphere suspension. The reaction with $NaBH_4$ continued for 3 hours at 4° C., at which time the microspheres were washed as described in Example 1. The aldehyde content of these coated microspheres decreased from 2.9 millimole/g microspheres to 2.3 millimole/g microspheres.

EXAMPLE 13

Examples 10 to 12 were repeated substituting $PdCl_2$ for $H_2PtCl_6$. The resulting black, palladium coated microspheres have similar aldehyde contents, respectively, to those of Examples 10 to 12.

EXAMPLE 14

Examples 10 to 13 were repeated substituting for the "alkaline" polyacrolein microspheres of $1\mu$ diameter the following polyaldehyde microspheres: "alkaline" polyacrolein microspheres of $0.1\mu$ and $5\mu$ diameters, "irradiated" polyacrolein microspheres of $0.1\mu$ average diameter, polyglutaraldehyde microspheres of $0.4\mu$ average diameter and agarose-polyacrolein microsphere beads of diameters ranging from $40\mu$ to $200\mu$ and from $800\mu$ to $1200\mu$. The microspheres were washed as described in Example 3. The aldehyde content of the resulted coated beads decreased proportionately as described in Examples 10 to 13.

EXAMPLE 15

100 mg "alkaline" polyacrolein microspheres ($3\mu$ diameter), in 5 ml $H_2O$ at pH 8.0 were shaken with 10 mg deferoxamine (an iron chelating compound) at 60° C. for 12 h. The microspheres were then washed by three centrifugations at 500 g for 10 minutes. The derivatized microspheres were then resuspended in 5 ml PBS or $H_2O$. Thereafter, 40 mg of ferric sulfate was added and the mixture was shaken at 4° C. for 1 hour. The resulting black microspheres were washed by three centrifugations at 500 g for 10 minutes, and then resuspended in 5 ml PBS or $H_2O$. Thereafter, 200 mg $NaBH_4$ were added and the mixture was shaken at 4° C. for 1 hour. The resulting black, microspheres were washed by three centrifugations at 500 g for 10 minutes, and then resuspended in 5 ml PBS or $H_2O$. The microspheres produced are very easily attracted to a magnet. Their aldehyde content decreased by $\frac{1}{3}$ as a result of the coating process.

EXAMPLE 16

Example 15 was repeated substituting for the 10 mg deferoxamine and the 40 mg ferric sulfate, 150 mg of the same compounds. The resulting microspheres possessed higher iron content; their aldehyde content decreased by $\frac{1}{2}$ as a result of the coating process.

EXAMPLE 17

Example 15 was repeated substituting for the deferoxamine and the ferric sulfate, hexane diamine brought to pH 7.0 with HCl, and $PdCl_2$, respectively. The aldehyde content of the resulting palladium coated microspheres decreased during the process from 2.9 millimole/g microspheres to 2.1 millimole/g microspheres.

EXAMPLE 18

Example 17 was repeated substituting for pH 7.0 for the binding between hexandiamine and the microspheres, pH 3.0 or pH 11.0. The coated microspheres so produced had a similar aldehyde content to those described in Example 17.

EXAMPLE 19

Example 17 was repeated substituting for $PdCl_2$ other metal compounds of the transition elements such as, Au (radioactive and not radioactive), Tc (radioactive and not radioactive), Pt, Ni and Co. The aldehyde content of the resulting coated microspheres decreased proportionately as described in experiment 17.

EXAMPLE 20

Examples 17 and 19 were repeated substituting for the hexane diamine, polyethylene imine or N,N-diethylethylenediamine. The coated microspheres so produced had a similar aldehyde content to those described in experiments 17 and 19.

EXAMPLE 21

Examples 15 to 20 were repeated substituting for the "alkaline" polyacrolein microspheres of $3\mu$ diameter other polyaldehyde microspheres, e.g. "alkaline" polyacrolein microspheres of $1\mu$ and $0.05\mu$ diameters, "redox" polyacrolein microspheres of $0.1\mu$ average diameter, polyglutaraldehyde microspheres of $0.4\mu$ average diameter and agarose-polyacrolein microsphere beads of diameters ranging from 40 to $200\mu$ and from $800\mu$ to $1200\mu$. The microspheres were washed as described in Example 3. The aldehyde content of the resulting metal coated microspheres decreased proportionately as described in experiments 15 to 20.

EXAMPLE 22

BINDING OF AMINO LIGANDS

Gold coated "alkaline" polyacrolein microspheres (50 mg in 2.5 ml PBS) prepared as described in Example 1 were shaken with 10 mg of either bovine serum albumin (BSA) or goat IgG at room temperature for 12 hours. Unbound protein was removed by four centrifugations at 500 g for 10 minutes. The binding capacity of these coated microspheres towards BSA and goat IgG, as measured by the method of Lowry et al., J. Biol. Chem 192:265-275(1951) was found to be 10 mg/g microspheres and 28 mg/g microspheres, respectively.

EXAMPLE 23

Experiment 22 was repeated substituting for the gold coated "alkaline" polyacrolein microspheres, gold coated "redox" polyacrolein microspheres. The binding capacity of the coated microspheres towards the proteins was found to be 25 mg BSA/g microspheres and 60 mg goat IgG/g microspheres.

EXAMPLE 24

Experiments 22 and 23 were repeated substituting for the gold coated microspheres the platinum coated microspheres. The binding capacity of the platinum coated microspheres towards the proteins was similar to the binding capacity obtained in Examples 22 and 23.

EXAMPLE 25

Labeling of Mouse Splenocytes.

Gold containing "alkaline" polyacrolein microspheres of $0.1\mu$ average diameter were shaken for 2 hours, at 4° C., with goat anti-mouse IgG (GaMIgG) (0.5 mg microspheres, 30 $\mu$g GaMIgG in a total volume of 0.1 ml PBS). Unbound antibody was then separated by passing the microsphere suspension through a sepharose 4B column. The free aldehyde groups were then quenched with 1% (w/v) BSA for 3 hours at 4° C. The GaMIgG derivatized microspheres were then added to PBS solution containing $10^6$ normal mouse splenocytes and the mixture was shaken at 40° C. for 1 hour. The cells were then separated from unreacted derivatized microspheres by three centrifugations at 500 g for 10 minutes. The cells were then resuspended in PBS and were examined under a fluorescent microscope. The labeled cells had a dark red color. Approximately, 95% of the unlabeled cells were T cells as was determined with a fluorescent anti-Thy 1.2 antibody. Scanning electron microscopy photomicrographs of the labeled cells could be obtained without a gold coating on the microspheres.

EXAMPLE 26

Separation of Human Red Blood Cells (RBC) from Turkey RBC.

Iron coated polyacrolein microspheres of $2\mu$ average diameter were shaken for 2 hours, at 4° C., with purified goat anti rabbit IgG (GaRIgG) (1 mg microspheres, 0.1 mg GaRIgG in total volume of 0.15 ml PBS). Thereafter unbound antibody was removed by passing the microsphere suspension through a Sepharose 4B column. The separation was monitored by measuring spectrophotometrically the absorbance at 280 nm. The free aldehyde groups of the microsphere antibody conjugate were quenched with 2% (w/v) bovine serum albumin solution for several hours at 4° C.

A mixture containing $10^6$ human RBC and $10^6$ turkey RBC were shaken for 50 min. at 4° C. with rabbit anti human RBC ($10^6$ human RBC with 0.8 $\mu$g rabbit anti human RBC antibodies in 0f.1 ml PBS solution). The cells were then separated and washed 4 times by spinning the cell suspension at 500 g for 10 min. The goat anti rabbit derivatized microspheres were then added to the cell mixture and the mixture was shaken at 4° C. for 1 hour. The cells were then separated from unreacted derivatized microspheres by centrifugation 3 times at 500 g for 10 min. and resuspended in PBS solution. Then, a small magnet was fitted on the outside wall of a vial containing the PBS solution of the cell mixture. After 15 minutes, cells which were not attracted to the wall were isolated. The attracted cells were resuspended in PBS and the magnetic separation was repeated twice. Examination with light microscopy showed that more than 95% of the attracted cells were human RBC.

EXAMPLE 27

Diagnostics Purposes

Antibodies bound to metal coated polyaldehyde microspheres were used for the detection of appropriate antigens. The technique is based on agglutination, due to an immune reaction between the bound antibody and the appropriate antigen, resulting in color reduction.

Gold containing "alkaline" polyacrolein microspheres of 400 Å diameter conjugated to rabbit anti-human chorionic gonadotropin (RaHCG) were diluted with PBS to obtain an absorbance $A_{540\,nm}^{1\,cm} = 2.0$. The absorbance spectrum of this conjugate does not change significantly during incubation periods of at least 4 hours. 1 ml of the buffered conjugate was added to 0.15 ml of a standard HCG solution in urine. The mixture was mixed and after an incubation time of 2 hours at room temperature the decrease in the absorbance at $A_{540\,nm}^{1\,cm}$ of a 0.1 ml aliquot was measured. The useful measuring range is between 60 and 2000 IU/l HCG.

EXAMPLE 28

Catalysis

Hydrogenation of 600 mg of the platinum coated "alkaline" polyacrolein microspheres of 0.1µ diameter (containing 25% (w/v) platinum) in 100 ml ethanol was achieved at room temperature and atmospheric pressure. 100 ml $H_2$ were absorbed by the microspheres, indicating the initial presence of 4.5 millimole of double bond in 600 mg of the coated microspheres. A similar double bond content was obtained by performing the hydrogenation of 450 mg of uncoated "alkaline" polyacrolein microsphered of 0.1µ diameter in the presence of 150 mg platinum black. Hydrogenation was not achieved, however, in the absence of platinum black.

EXAMPLE 29

Coating

A suspension of gold containing polyacrolein microspheres (1µ diameter, crosslinked, containing 20% w/w gold) was evaporated to dryness. A strong, flexible film of gold containing microspheres was thus formed.

EXAMPLE 30

Coating

A methylene chloride solution (25% w/w) of gold containing polyacrolein microspheres (as in Example 20) and polyvinyl chloride (PVC) (25% w/w) was cast on a glass surface. Evaporation of the solvent to dryness resulted in a PVC-gold microsphere coating.

What is claimed is:

1. A metal-coated polyaldehyde microsphere comprising a preformed polyaldehyde microsphere coated with a transition metal in elemental form, the transition metal being bound to the preformed polyaldehyde microsphere by either direct bonding to the aldehyde groups of the microsphere or by ionic or coordinate bonding to primary amines which are covalently bound to the aldehyde groups of the microsphere.

2. A metal-coated polyaldehyde microspheres of claim 1, wherein the polyaldehyde is polyacrolein or polyglutaraldehyde.

3. A metal-coated polyaldehyde microsphere of claim 1, wherein the transition metal is gold, silver, platinum, palladium, technetium, iron, nickel or cobalt.

4. A metal-coated polyaldehyde microsphere of claim 1, wherein the transition metal is a radioactive isotope.

5. A metal-coated polyaldehyde microsphere of claim 1, wherein the metal is magnetic.

6. A metal-coated polyaldehyde microsphere of claim 1, which additionally has a compound having at least one primary amine group bound to its surface.

7. A metal-coated polyaldehyde microsphere of claim 6, wherein the compound is a drug, antibody, antigen, enzyme, or other protein.

8. A metal-coated polyaldehyde microsphere of claim 7, wherein the compound is an antibody.

9. An agarose-encapsulated, metal-coated polyaldehyde microsphere comprising a preformed polyaldehyde microsphere coated with a transition metal in elemental form, the transition metal being bound to the preformed polyaldehyde microsphere by either direct bonding to the aldehyde groups of the microsphere or ionic or coordinate bonding to primary amines which are covalently bound to the aldehyde groups of the microsphere, encapsulated in agarose.

* * * * *